(12) United States Patent
Qiu

(10) Patent No.: US 7,659,530 B2
(45) Date of Patent: Feb. 9, 2010

(54) FOCUSING AND SHIELDING DEVICE FOR ENCEPHALIC PHOTON KNIFE

(76) Inventor: Yanxiong Qiu, Block B, Buld. B1, Shenzhen Digital Technical Yard, South Road 7th, High-Tech Zhon, Shenzhen (CN)

( * ) Notice: Subject to any disclaimer, the term of this patent is extended or adjusted under 35 U.S.C. 154(b) by 279 days.

(21) Appl. No.: 11/831,321

(22) Filed: Jul. 31, 2007

(65) Prior Publication Data

US 2008/0029719 A1 Feb. 7, 2008

(30) Foreign Application Priority Data

Aug. 3, 2006 (CN) .................... 2006 2 0123407
Aug. 3, 2006 (CN) .................... 2006 2 0123408

(51) Int. Cl.
*G21F 3/00* (2006.01)

(52) U.S. Cl. .............. 250/515.1; 250/492.1; 250/493.1; 250/505.1; 250/516.1; 378/145; 378/147; 378/148; 378/149; 378/150; 600/427

(58) Field of Classification Search .............. 250/505.1, 250/515.1, 492.1, 493.1, 516.1; 378/145, 378/147, 148, 149, 150; 600/427
See application file for complete search history.

(56) References Cited

U.S. PATENT DOCUMENTS

| 5,448,611 | A | * | 9/1995 | Kerjean ...................... 378/65 |
| 5,528,653 | A | * | 6/1996 | Song et al. .................. 378/65 |
| 5,627,870 | A | * | 5/1997 | Kopecky ..................... 378/65 |
| 5,757,886 | A | * | 5/1998 | Song .......................... 378/147 |
| 6,044,126 | A | * | 3/2000 | Rousseau et al. ........... 378/65 |
| 6,201,988 | B1 | * | 3/2001 | Bourland et al. ........... 600/427 |
| 6,763,588 | B1 | * | 7/2004 | Nilsson et al. ............. 29/896.6 |
| 6,931,096 | B2 | * | 8/2005 | Carlsson et al. ............ 378/65 |
| 6,968,036 | B2 | * | 11/2005 | Carlsson et al. ............ 378/65 |
| 7,302,037 | B1 | * | 11/2007 | Helenowski ................ 378/65 |

* cited by examiner

*Primary Examiner*—David A Vanore
*Assistant Examiner*—Michael J Logie
(74) *Attorney, Agent, or Firm*—Global IP Services; Tianhua Gu

(57) ABSTRACT

A focusing and shielding device for encephalic photon knife consisting of a body of ray source, a switch and an armet, the ray source body is a hemispherical shell with certain thickness, a ray source cavity for placing ray source and a pre-collimation hole are defined on the hemispherical shell; the ray source cavity is defined on the outer surface of the hemispherical shell, and the pre-collimation hole is define on the inner surface of the hemispherical shell and connecting with the ray source cavity; the switch is defined inside the body of the ray source, and the outer surface of the switch is in hemispherical shape, a middle collimation hole is set on the switch; the armet is deposited inside the switch, and the inner surface is in columnar shape, an end collimation hole is defined on the armet, a therapy path is defined where the middle collimation hole connected with the pre-collimation hole to form the end collimation hole. The focusing and shielding device for encephalic photon knife of the present invention is simple in structure and low in cost, and as the inner surface of the armet is in a column shape, it expand the space for therapy.

6 Claims, 4 Drawing Sheets

FOCUSING AND SHIELDING DEVICE FOR ENCEPHALIC PHOTON KNIFE

CROSS REFERENCE TO RELATED PATENT APPLICATION

This patent application claims the priorities of the Chinese patent application No. 200620123407.4, filing date of Aug. 3, 2006 and the Chinese patent application No. 200620123408.9, filing date of Aug. 3, 2006.

FIELD OF THE INVENTION

The present invention relates to a focusing and shielding device for photon knife, more particularly, a focusing and shielding device for encephalic photon knife.

BACKGROUND OF THE INVENTION

A Swedish professor, Leksell, first presented a concept of "Stereotactic Radiosurgery" (SRS), is using the theory of stereotaxic to apply high-octane ray focusing irradiation and to destroy target organisms, thus to cure the sickness. The edges of the treated portion cured by the apparatus of radiosurgery is clear and plain, such as be cut by a knife, it is so called as "photon knife".

The people who skilled in the art will easily recognize that the therapy efficiency is correlative with the space for treatment, the strength of the radial, the focusing degree and the shielding correlative. In order to match such requirements, the photon knife of the prior art is complicated in configuration and high in cost that restrict its popularization.

SUMMARY OF THE INVENTION

In order to overcome the defects of complicated in configuration and high in cost of the photon knife in the prior art, the object of this invention is to provide a focusing and shielding device for encephalic photon knife with more therapeutic space, which is simplify in structure and low in cost. The technical solution for this invention is, a focusing and shielding device for encephalic photon knife, consisting of a body of ray source, a switch and an armet, wherein;

the ray source body is a hemispherical shell with certain thickness, a ray source cavity for placing ray source and a pre-collimation hole are defined on the hemispherical shell; the ray source cavity is defined on the outer surface of the hemispherical shell, and the pre-collimation hole is define on the inner surface of the hemispherical shell and connecting with the ray source cavity;

the switch is defined inside the body of the ray source, and the outer surface of the switch is in hemispherical shape, a middle collimation hole is set on the switch;

the armet is deposited inside the switch, and the inner surface is in columnar shape, an end collimation hole is defined on the armet, a therapy path is defined where the middle collimation hole connected with the pre-collimation hole to form the end collimation hole.

Preferably, the inner surface of the switch is in hemispherical shape, which is the same shape as the outer surface of the armet.

Preferably, the inner surface of the switch is in columnar shape, which is the same shape as the outer surface of the armet.

Preferably, the body of ray source and the switch can turn correspondingly to each other to shut down the therapy path.

The focusing and shielding device for encephalic photon knife of the present invention has the advantages of: as the inner surface of the armet is in a columnar shape, the whole head of the patient can be placed inside the armet to conduct the operation; and as the therapy path can be shut down by turning the switch, it decreases the radiation that takes to the patient; further, the device is simple in structure and low in cost.

BRIEF DESCRIPTION OF THE INVENTION

DETAILED DESCRIPTION OF THE PREFERRED EMBODIMENT

Figure 1:
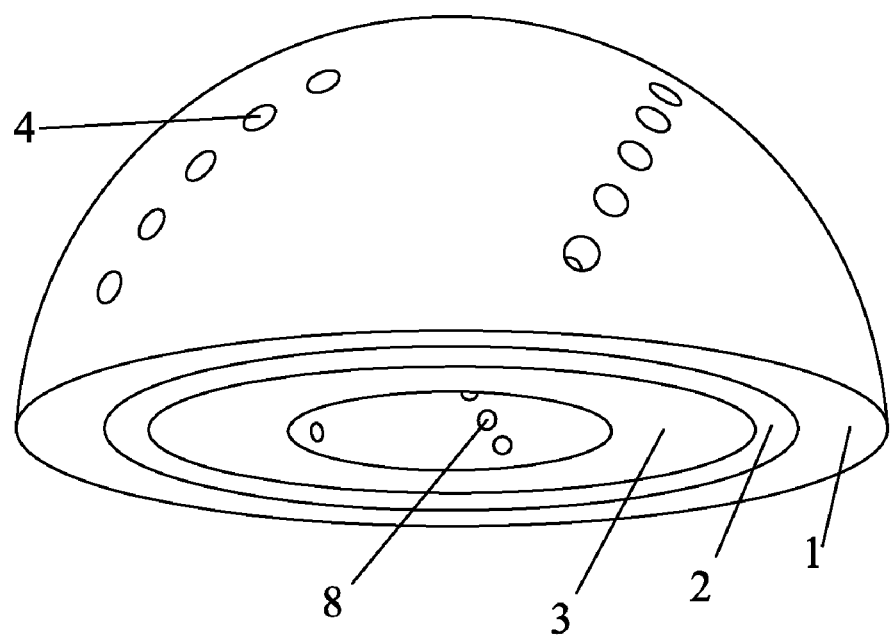
FIG. 1 is the schematic view of one preferred embodiment of the focusing and shielding device for encephalic photon knife, in accordance with the present invention.
Figure 2:
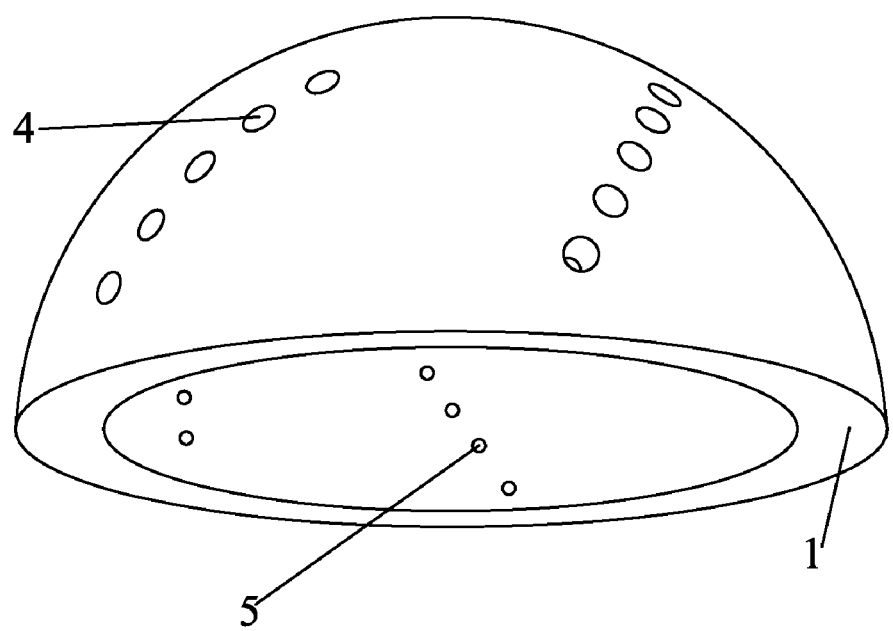
FIG. 2 to FIG. 4 are the schematic views of the body of ray source, switch, and armet as in FIG. 1 respectively.
Figure 3:
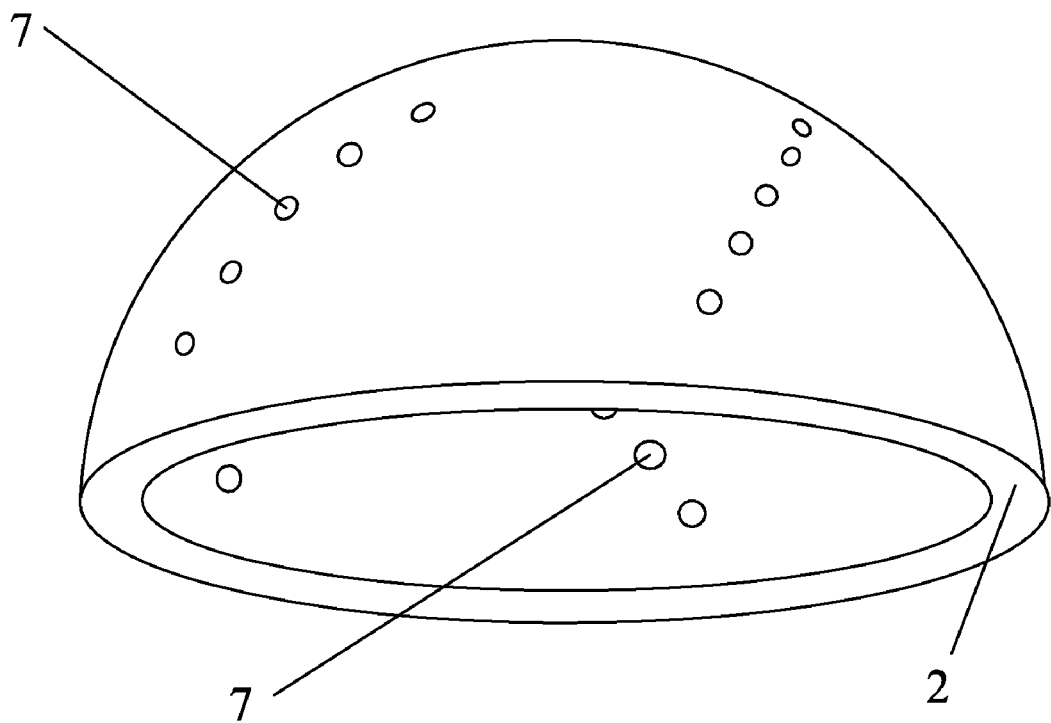
Figure 4:
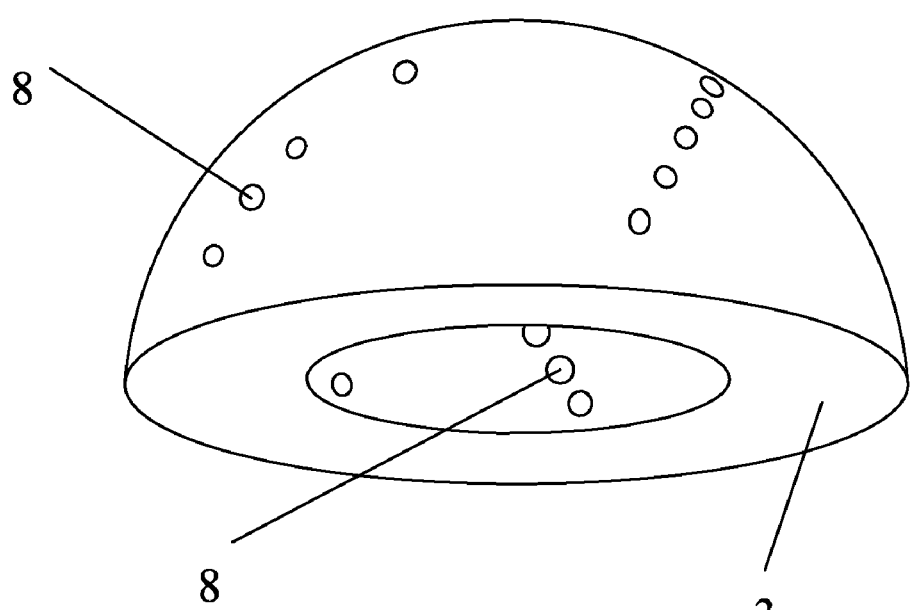
Figure 5:
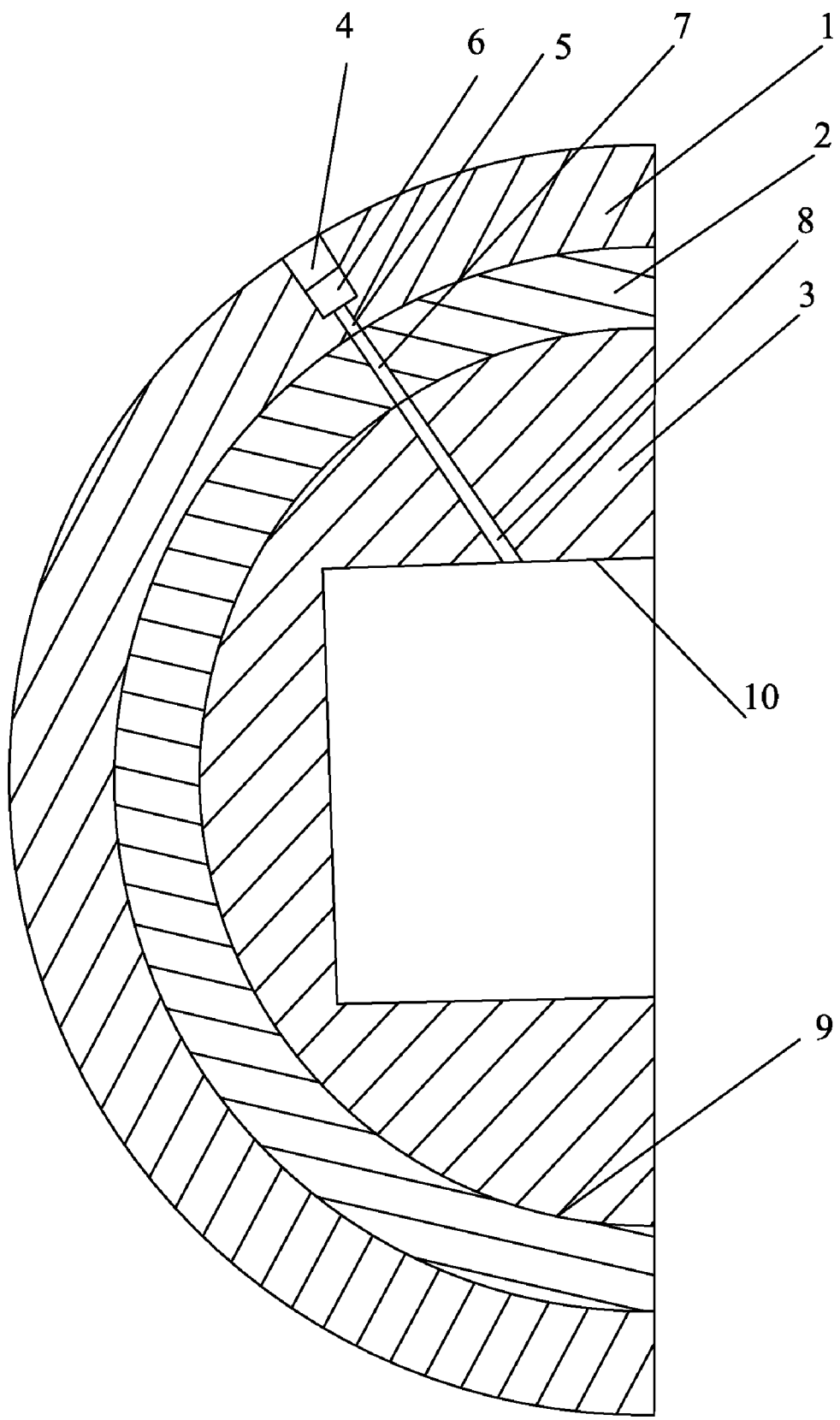
FIG. 5 is the sectional view of the embodiment of the focusing and shielding device for encephalic photon knife as in FIG. 1.

A preferred embodiment of the present invention is showed in FIG. 1 to FIG. 5, wherein, FIG. 1 is the perspective view, FIG. 2 to FIG. 4 are the schematic views of the body of ray source, switch, and armet respectively, and FIG. 5 is the sectional view. As shown in FIGS. 1-5, the focusing and shielding device for encephalic photon knife of the present invention consisting of a body of ray source 1, a switch 2 and an armet 3; the ray source body 1 is a round shell with certain thickness, a ray source cavity 4 and a pre-collimation hole 5 are defined on the body of ray source 1, and the ray source cavity 4 and pre-collimation hole 5 are connected with each other, the ray source 6 is placing inside the ray source cavity 4. A middle collimation hole 7 is set on switch 2; the armet 3 is deposited inside the switch, and an end collimation hole 8 is defined on the armet 3, the outer surface 9 of the armet 3 is with the same shape of hemispheroid as to the shape of the inner surface of the switch, and the inner surface 10 of the armet is in columnar shape.

In the present embodiment, the switch 2 and body of ray source 1 can turn correspondingly to each other. When the switch 2 turns to a certain angle, the pre-collimation hole 5, middle collimation hole 7 and the end collimation hole 8 are connected, thus to form a therapy path; and when the switch 2 turns to another angle, the pre-collimation hole 5 and end collimation hole 8 will not connect then, and the therapy path is shut down.

Figure 6:
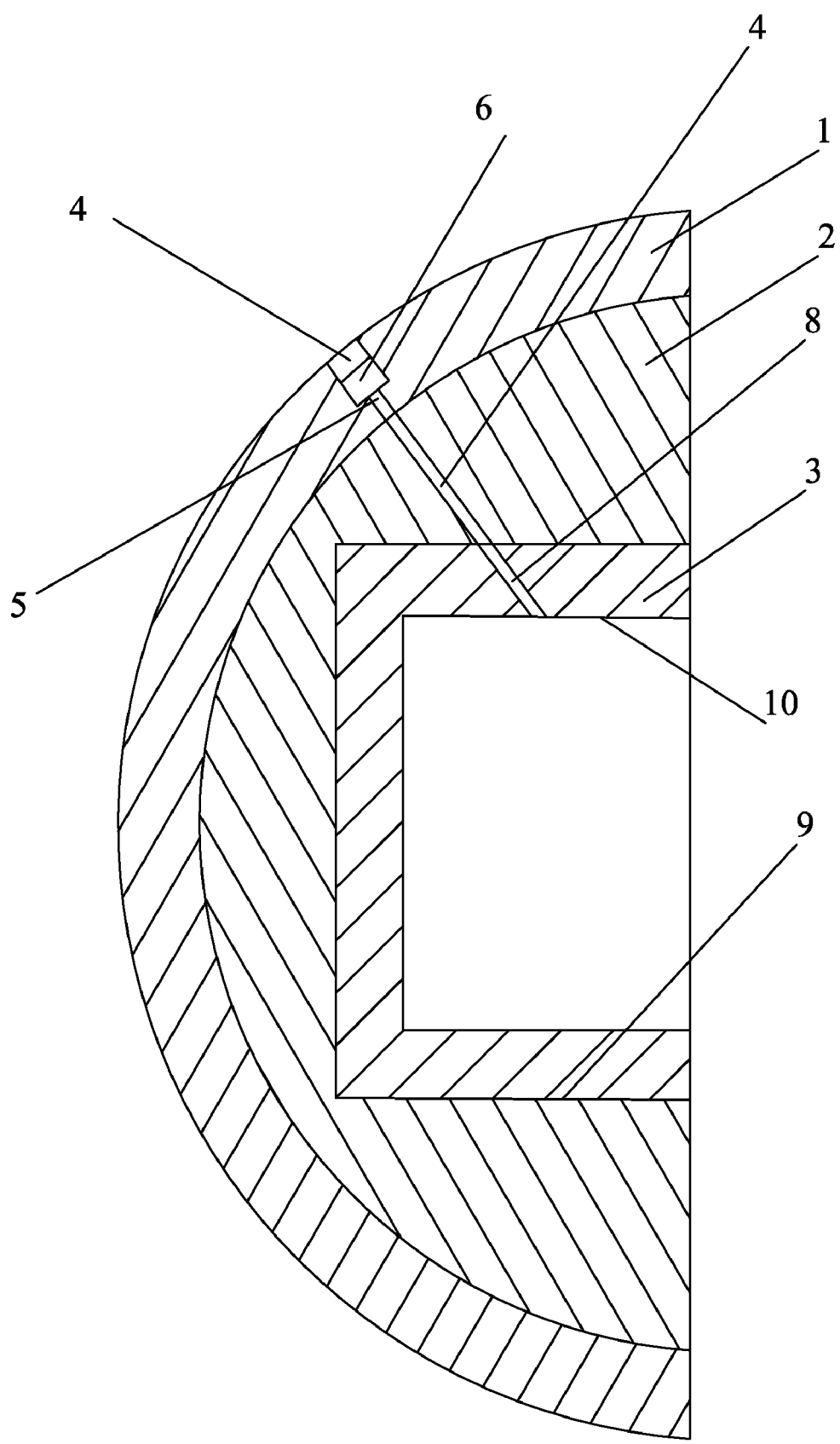
FIG. 6 is the sectional view of another embodiment of the focusing and shielding device for encephalic photon knife.

FIG. 6 is another embodiment of the focusing and shielding device for encephalic photon knife, in accordance with the present invention. In this embodiment, the outer surface of the switch 2 is in hemisphere shape and the inner surface is in columnar shape; and both the inner surface and outer surface of the armet are in columnar shape.

With the above mentioned technical solution, the focusing and shielding device for encephalic photon knife of the present invention is simple in structure and low in cost, and as the inner surface of the armet is in a columnar shape, it expand the space for therapy, the whole head of the patient can be placed inside the armet to conduct the operation.

Throughout the specification the aim has been to describe the preferred embodiment of the present invention without limiting the invention to any one embodiment or specific collection of features. Persons skilled in the relevant art may realize variations from the specific embodiment that will nonetheless fall within the scope of the invention.

What is claimed is:

1. A focusing and shielding device for an encephalic photon knife, comprising a ray source body, a switch and an armet; said ray source body being a hemispherical shell with a certain thickness having a ray source cavity for placing a ray source and a pre-collimation hole for collimating a ray; said ray source cavity being defined on an outer surface of the hemispherical shell, and said pre-collimation hole being defined on an inner surface of the hemispherical shell and connected with said ray source cavity;

said switch is defined inside the body of said ray source, and an outer surface of said switch being hemispherical shape, a middle collimation hole being set on the switch;

said armet being deposited inside said switch, an inner surface of said armet is in a columnar shape, an end collimation hole being defined on said armet;

a therapy path being defined when said middle collimation hole connecting said pre-collimation hole with said end collimation hole together.

2. The focusing and shielding device for an encephalic photon knife of claim 1, wherein an inner surface of said switch is in hemispherical shape, and is the same shape as an outer surface of the armet.

3. The focusing and shielding device for an encephalic photon knife of claim 2, wherein said ray source body and said switch can be turned correspondingly to each other to shut down said therapy path.

4. The focusing and shielding device for an encephalic photon knife of claim 1, wherein an inner surface of said switch is in columnar shape, and is the same shape as an outer surface of said armet.

5. The focusing and shielding device for an encephalic photon knife of claim 4, wherein said ray source body and said switch can be turned correspondingly to each other to shut down said therapy path.

6. The focusing and shielding device for an encephalic photon knife of claim 1, wherein said ray source body and said switch can be turned correspondingly to each other to shut down said therapy path.

* * * * *